United States Patent
Xu et al.

(10) Patent No.: US 11,058,346 B2
(45) Date of Patent: Jul. 13, 2021

(54) OPTICAL IMAGING METHOD BASED ON MAPPING OF LAYERED STRUCTURE

(71) Applicant: WENZHOU MEDICAL UNIVERSITY, Wenzhou (CN)

(72) Inventors: Min Xu, Wenzhou (CN); Bixin Zeng, Wenzhou (CN); Xinlin Chen, Wenzhou (CN)

(73) Assignee: WENZHOU MEDICAL UNIVERSITY, Wenzhou (CN)

( * ) Notice: Subject to any disclaimer, the term of this patent is extended or adjusted under 35 U.S.C. 154(b) by 0 days.

(21) Appl. No.: 16/760,378

(22) PCT Filed: Nov. 30, 2017

(86) PCT No.: PCT/CN2017/113691
§ 371 (c)(1),
(2) Date: Aug. 6, 2020

(87) PCT Pub. No.: WO2019/085113
PCT Pub. Date: May 9, 2019

(65) Prior Publication Data
US 2020/0383630 A1     Dec. 10, 2020

(30) Foreign Application Priority Data

Oct. 30, 2017   (CN) .......................... 201711038893.9

(51) Int. Cl.
*A61B 5/00* (2006.01)

(52) U.S. Cl.
CPC ............ *A61B 5/443* (2013.01); *A61B 5/0075* (2013.01); *A61B 5/72* (2013.01); *A61B 5/0077* (2013.01)

(58) Field of Classification Search
CPC ..... A61B 5/443; A61B 5/0075; A61B 5/0077; A61B 5/145
See application file for complete search history.

(56) References Cited

U.S. PATENT DOCUMENTS 9,551,656 B2    1/2017  Xu et al.
2009/0306520 A1  12/2009 Schmitt et al.
(Continued)

FOREIGN PATENT DOCUMENTS

| CN | 102046071 A | 5/2011 |
| CN | 102883658 A | 1/2013 |

(Continued)

*Primary Examiner* — Eric F Winakur
*Assistant Examiner* — Abid A Mustansir
(74) *Attorney, Agent, or Firm* — Christensen, Fonder, Dardi & Herbert PLLC

(57) ABSTRACT

An optical imaging method based on mapping of a layered structure. The specific spatial distribution and optical properties of materials in each layer are fully taken into account so that optical information of each corresponding layer can be separated out, wherein the optical information comprises absorption and scattering coefficients of each layer. The method is applied to biological system detection to obtain physiological parameter information of each layer of tissue, wherein the physiological parameter information comprises the content of oxyhemoglobin, the content of deoxyhemoglobin the content of melanin, and epidermal thickness. The method in combination with SFDI technology is applied to forearm reactive hyperemia experiments and skin mole examinations yielding positive results.

6 Claims, 17 Drawing Sheets
(17 of 17 Drawing Sheet(s) Filed in Color)

(56) References Cited

U.S. PATENT DOCUMENTS

| | | |
|---|---|---|
| 2011/0124988 A1 | 5/2011 | Cuccia |
| 2014/0128744 A1 | 5/2014 | Cuccia et al. |
| 2014/0213910 A1 | 7/2014 | Durkin et al. |
| 2015/0223749 A1 | 8/2015 | Park et al. |
| 2017/0135616 A1 | 5/2017 | Sato |

FOREIGN PATENT DOCUMENTS

| | | |
|---|---|---|
| CN | 104825131 A | 8/2015 |
| CN | 105136690 A | 12/2015 |
| CN | 106163399 A | 11/2016 |

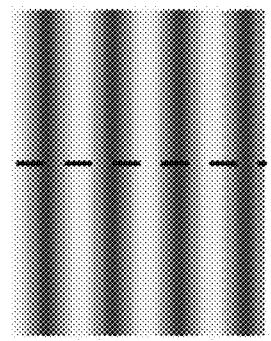 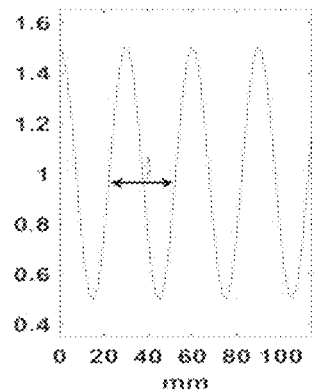
Fig. 2a              Fig. 2b
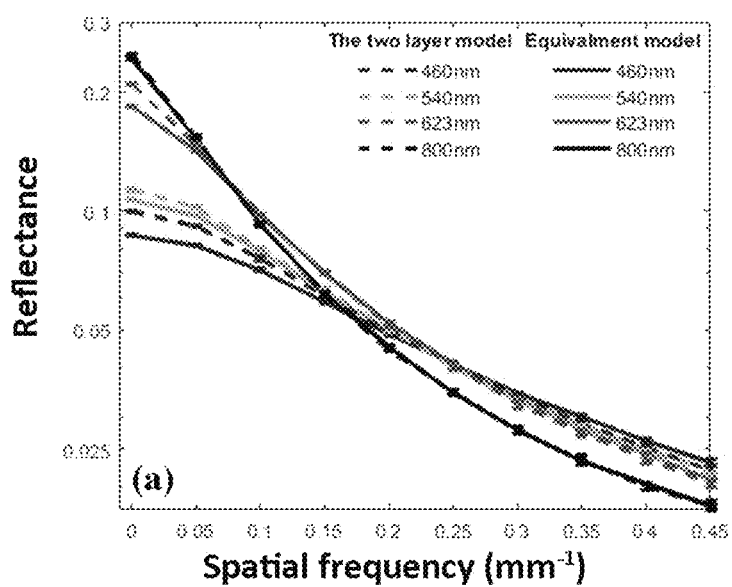
Fig. 3a

Melanin

Epidermal thickness

OPTICAL IMAGING METHOD BASED ON MAPPING OF LAYERED STRUCTURE

RELATED APPLICATIONS

The present application is a National Phase entry of PCT Application No. PCT/CN2017/113691, filed Nov. 30, 2017, which claims priority to Chinese Patent Application No. 201711038893.9, filed Oct. 30, 2017, the disclosures of which are hereby incorporated by reference herein in their entirety.

FIELD OF THE INVENTION

The invention particularly relates to an optical imaging method based on a mapping of layered structure.

BACKGROUND OF THE INVENTION

In the field of optical imaging, the composition of biological tissues is complex and diverse, while all the detected substances are not isotropic substances. In fact, the biological tissues are anisotropic substances, and the detected regional substances are spatially and unevenly distributed (such as melanin of skin exists only in the epidermis, and oxyhemoglobin and deoxyhemoglobin exist in the dermis), but in actual treatment, in order to simplify the actual path of the light entering the biological tissue, the detected substance is considered to be an isotropic substance, so that the substance content of each layer can be misestimated, and the spatial distribution, optical and physiological information of the detected substance cannot be accurately reduced. The large-area skin imaging method based on a mapping of layered structure fully considers the actual path of light entering biological tissues and the spatial distribution mode of measured substances. The spatial distribution, optical information and physiological information of the detected substance can be accurately obtained.

SUMMARY OF THE INVENTION

In order to solve the technical problem, the invention provides an optical imaging method based on a mapping of layered structure.

The invention provides an optical imaging method based on a mapping of layered structure, mapping a layered structure to an equivalent uniform medium, wherein each layer of the layered structure has a respective absorption coefficient, the equivalent uniform medium having the same scattering characteristic as the layer, and the absorption coefficient being determined by a spatial modulation frequency of incident light and the absorption coefficient and thickness of each layer;

after obtaining optical parameters of the equivalent uniform medium in different incident light spatial modulation states by using transmission model of light in uniform medium, the scattering characteristic of medium and the absorption coefficient and thickness of each layer being inversely solved.

The layered structure is a bilayer layered structure or a multilayer layered structure.

Use of the optical imaging method based on a mapping of layered structure as described in skin parameter detection.

The use comprising the steps of:

I. acquiring optical parameters of corresponding layers through a large-area optical imaging method of a layered model, wherein the mapping of layered structure comprises the following steps of (1) the absorption coefficients of epidermis and dermis being established $$\mu_{a,epidermis}(\lambda) = \varepsilon_{melanin}(\lambda) c_{melanin}$$

$$\mu_{a,dermis}(\lambda) = \varepsilon_{Hb}(\lambda) c_{Hb} + \varepsilon_{HbO_2}(\lambda) c_{HbO_2},$$

wherein $c_{HbO_2}$, $c_{Hb}$ and $c_{melanin}$ are concentrations of oxyhemoglobin, deoxyhemoglobin and melanin respectively, $\varepsilon_{HbO_2}$, $\varepsilon_{Hb}$ and $\varepsilon_{melanin}$ are molar extinction coefficients of oxyhemoglobin, deoxyhemoglobin and melanin respectively, and $\lambda$ is wavelength;

(2) establishing the following relationship $$\mu_a(q,\lambda) L(q,\lambda) = \mu_{a,epidermis}(\lambda) h + \mu_{a,dermis}(\lambda)(L-h),$$

wherein q is incident light spatial modulation angular frequency, $\mu_a(q,\lambda)$ is the absorption coefficient of the equivalent uniform medium, h is epidermal thickness, and an average depth of detection $$L(q,\lambda) = \frac{(1+Ql)^2(2\mu_t')^{-2} + (1+\mu_t'l)^2(2Q)^{-2} - 2(1+Ql)(1+\mu_t'l)(Q+\mu_t')^{-2}}{(1+Ql)^2(2\mu_t')^{-1} + (1+\mu_t'l)^2(2Q)^{-1} - 2(1+Ql)(1+\mu_t'l)(Q+\mu_t')^{-1}}$$

wherein $\mu_t' = \mu^a + \mu_s'$, $Q = \sqrt{q^3 + 3\mu_a(\mu_a + \mu_s')}$, $D_0 = \frac{1}{3}\mu_s'$, l is extrapolated length, and $\mu_s'$ is reduced scattering coefficient;

(3) the absorption coefficient $\mu_a$ of the equivalent uniform medium being determined by step (2);

II. obtaining a content of each substance by Beer-Lambert law according to obtained optical parameters.

Use of an optical imaging method based on a mapping of layered structure as described in endoscopic tissue mucosal layer detection imaging.

An optical spectroscopic method based on a mapping of layered structure as described, mapping a layered structure to an equivalent uniform medium, wherein each layer of the layered structure has a respective absorption coefficient, the equivalent uniform medium having the same scattering characteristic as the layer, and the absorption coefficient being determined by a spatial modulation frequency of incident light and the absorption coefficient and thickness of each layer;

after obtaining optical parameters of the equivalent uniform medium in different incident light spatial modulation states by using transmission model of light in uniform medium, the scattering characteristic of medium and the absorption coefficient and thickness of each layer being inversely solved.

The invention has the beneficial effects that: the spatial distribution of biological tissues and the optical properties of each layer are fully considered, and the detection depth under the spatial modulation frequency of each wavelength is accurately evaluated, so that the spatial distribution of layered tissues and the material content of each layer can be accurately obtained, and the model is combined with the SFDI technology, and good results are obtained when the model is applied to forearm reactive hyperemia experiments and skin pigmented nevus detection.

BRIEF DESCRIPTION OF THE DRAWINGS

The patent application contains at least one drawing executed in color. Copies of this patent with color drawings will be provided by the Patent and Trademark Office upon request and payment of the necessary fee.

In FIGS. 2a and 2b, the left figure (FIG. 2a) is a spatial modulation pattern; the sinusoid of the right figure (FIG. 2b) is part of the spatial modulation pattern.

FIGS. 3a and 3b. FIG. 3a shows reflectance fitting of mapping model of layered structure and equivalent model, and error bars are the results after 5 fits. FIG. 3b shows that the maximum detection depths are 460 nm, 540 nm, 623 nm and 800 nm at different spatial frequencies.

DETAILED DESCRIPTION OF THE INVENTION

Embodiments of the present invention are further described below with reference to the accompanying drawings:

The invention provides an optical imaging method based on a mapping of layered structure, mapping a layered structure to an equivalent uniform medium, wherein each layer of the layered structure has a respective absorption coefficient, the equivalent uniform medium having the same scattering characteristic as the layer, and the absorption coefficient being determined by a spatial modulation frequency of incident light and the absorption coefficient and thickness of each layer;

after obtaining optical parameters of the equivalent uniform medium in different incident light spatial modulation states by using transmission model of light in uniform medium, the scattering characteristic of medium and the absorption coefficient and thickness of each layer being inversely solved.

The layered structure is a bilayer layered structure or a multilayer layered structure.

Figure 1:
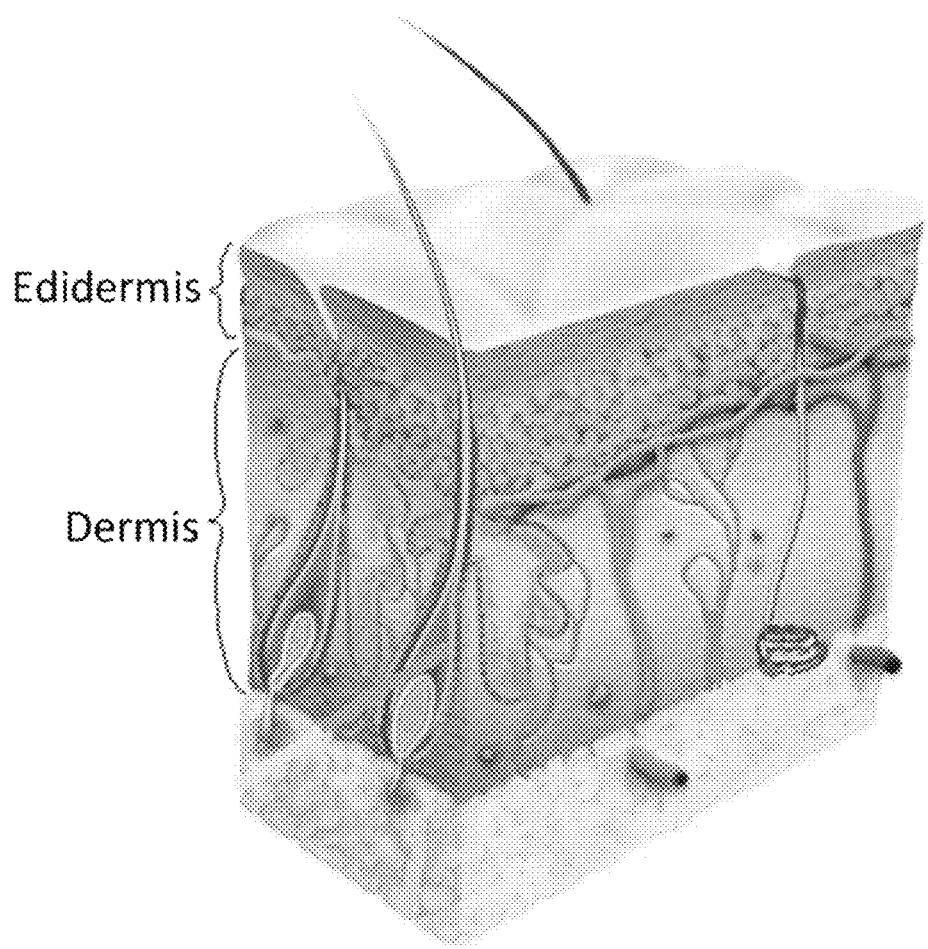
FIG. 1 is a schematic view of a skin structure.

The deduction of the optical imaging method based on a mapping of layered structure is explained by taking the skin as an example, and the structural characteristics of the skin are as follows: in a multilayer structure (FIG. 1), melanin is mainly concentrated in the epidermis (50-120 μm), and the epidermis (1-4 mm) is substantially free of blood. Oxyhemoglobin and deoxyhemoglobin content only exists in the dermis.

The epidermis of the skin is extremely thin, and it can be assumed that the epidermis and the dermis have the same scattering coefficient $\mu_s'$, and the absorption of light is different in different layers. The dominant one is the melanin of the epidermis, and the second dominant one is the oxyhemoglobin (HbO) and the deoxyhemoglobin (Hb) in the dermis. Assuming that the epidermal thickness is h, considering the detection depth of the spatial modulation frequency L=L(q), the frequency of the spatially modulated light q=2πf (FIGS. 2a and 2b).

The invention provides an optical imaging method based on a mapping of layered structure, which comprises the following steps:

I. acquiring optical parameters of corresponding layers through a large-area optical imaging method of a layered model, wherein the mapping of layered structure comprises the following steps of (1) the absorption coefficients of epidermis and dermis being established $$\mu_{a,epidermis}(\lambda) = \varepsilon_{melanin}(\lambda) c_{melanin}$$

$$\mu_{a,dermis}(\lambda) = \varepsilon_{Hb}(\lambda) c_{Hb} + \varepsilon_{HbO_2}(\lambda) c_{HbO_2},$$

wherein $c_{HbO_2}$, $c_{Hb}$ and $c_{melanin}$ are concentrations of oxyhemoglobin, deoxyhemoglobin and melanin respectively, $\varepsilon_{HbO_2}$, $\varepsilon_{Hb}$ and $\varepsilon_{melanin}$ are molar extinction coefficients of oxyhemoglobin, deoxyhemoglobin and melanin respectively, and λ is wavelength;

(2) establishing the following relationship $$\mu_a(q,\lambda) L(q,\lambda) = \mu_{a,epidermis}(\lambda) h + \mu_{a,dermis}(\lambda)(L-h),$$

wherein q is incident light spatial modulation angular frequency, $\mu_a(q,\lambda)$ is the absorption coefficient of the equivalent uniform medium, h is epidermal thickness, and an average depth of detection $$L(q,\lambda) = \frac{(1+Ql)^2(2\mu_t')^{-2} + (1+\mu_t'l)^2(2Q)^{-2} - 2(1+Ql)(1+\mu_t'l)(Q+\mu_t')^{-2}}{(1+Ql)^2(2\mu_t')^{-1} + (1+\mu_t'l)^2(2Q)^{-1} - 2(1+Ql)(1+\mu_t'l)(Q+\mu_t')^{-1}}$$

wherein $\mu_t' \equiv \mu_a + \mu_s'$, $Q \equiv \sqrt{q^3 + 3\mu_a(\mu_a+\mu_s')}$, $D_0 = \frac{1}{3}\mu_s'$, l is extrapolated length, and $\mu_s'$ is reduced scattering coefficient;

(3) the absorption coefficient $\mu_a$ of the equivalent uniform medium being determined by step (2);

II. obtaining a content of each substance by Beer-Lambert law according to obtained optical parameters.

Λ is 623 nm, 540 nm, 460 nm.

The image acquisition device is one or other of a CCD, a spectrometer or an optical fiber probe.

Figure 3B:
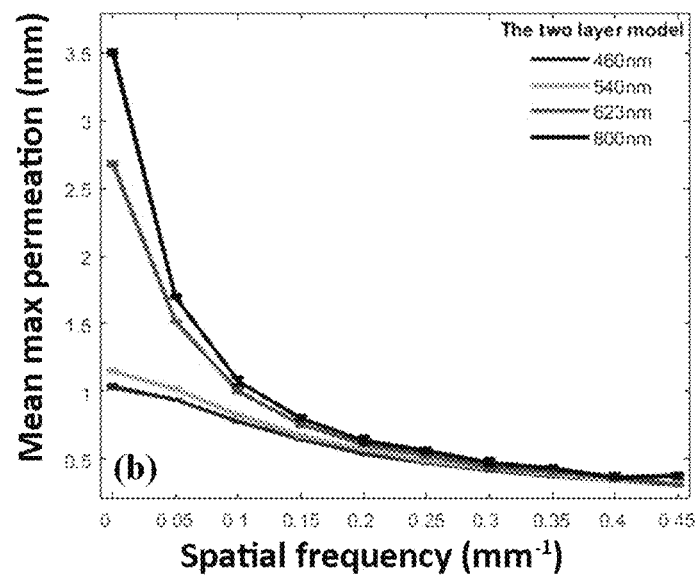

The mapping model of layered structure and Monte Carlo simulation of equivalent uniform medium are carried out. In the mapping model of layered structure, in 0.1 mm of epidermis, melanin content is 3.485 mM, while oxyhemoglobin and deoxyhemoglobin in dermis are 0.0077 mM 0.0027 mM respectively. The scattering coefficient at 540 nm is 1.7 mm$^{-1}$, the scattering capability is 0.76, the reflectivity is 1.4, and the anisotropy factor is 0.7. FIG. 3a shows comparison of diffuse reflectance for mapping model of layered structure and equivalent uniform model under Monte Carlo simulation. FIG. 3b shows the average maximum detection depth at each spatial frequency.

The optical imaging method based on a mapping of layered structure can also be applied to endoscopic tissue mucosal layer detection imaging.

The mapping of layered structure can also be applied in optical spectroscopy methods.

Application Example 1: Forearm Reactive Hyperemia Experiment

Experimental Protocol:

Real-time detection of the dorsal surface of an arm of a volunteer (n=6) is performed using a real-time single snap-shot multiple frequency demodulation—spatial frequency domain imaging (SSMD-SFDI) device. A digital micromirror device (DMD) projects a modulation pattern at wavelengths of 623 nm, 540 nm and 460 nm with a spatial frequency f=0.2. A detector (Point Grey Grasshop3 GS3-U3-51S5C) performs collection at a rate of 3 frames per second. Volunteers follow the following experimental protocol: 3 minutes of normal state, the pulse band generating pressure (200 mmg) for maintaining the arm for 4 minutes, the pulse band being released for resting for 3 minutes, performing collection for a total of 10 minutes, and direct-current and alternating-current information of the reflection pattern being rapidly demodulated by using an SSMD technology.

Figure 4A:
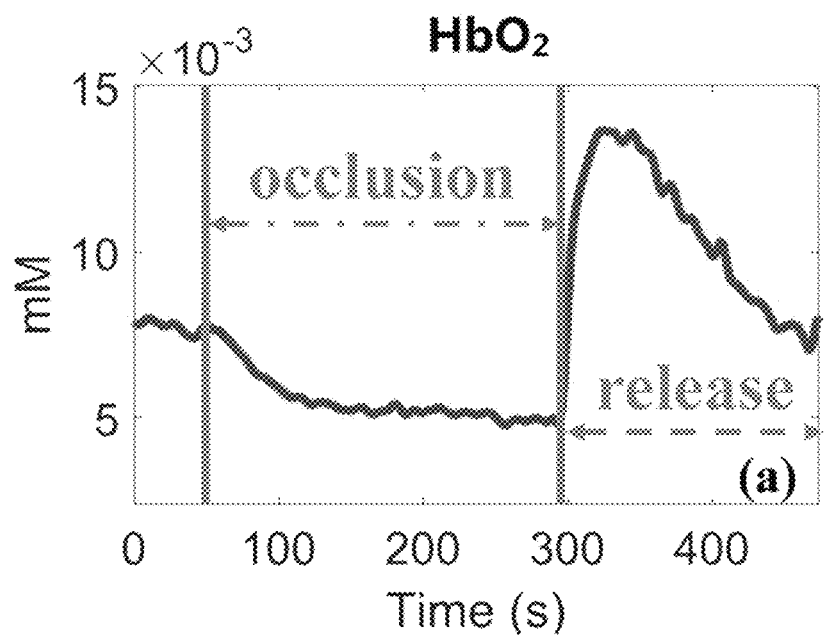
FIG. 4a is a schematic view showing the oxyhemoglobin concentration.
Figure 4B:
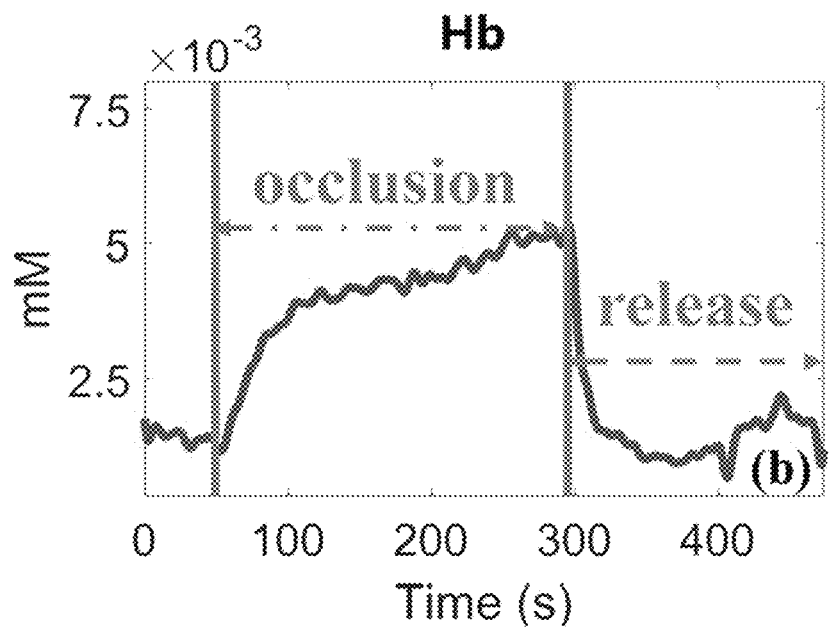
FIG. 4b depicts a deoxyhemoglobin concentration.
Figure 4C:
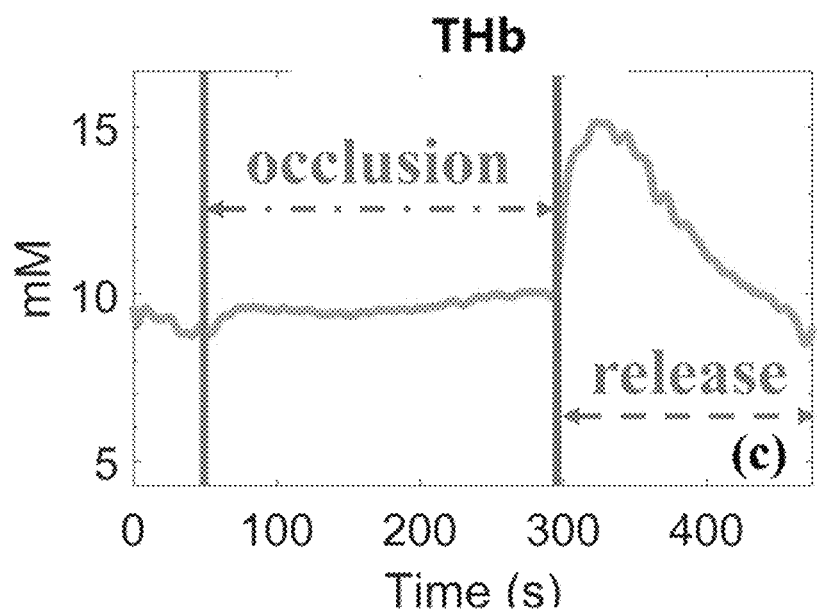
FIG. 4c depicts total hemoglobin concentration.
Figure 4D:
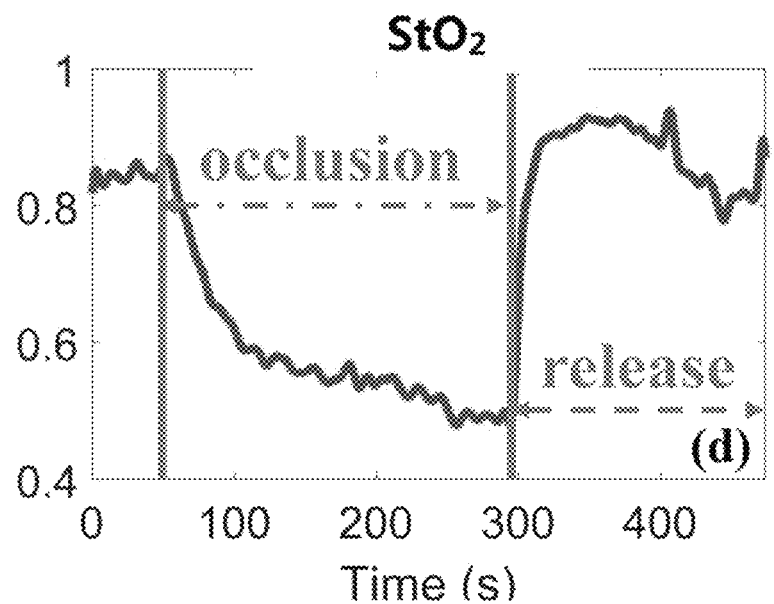
FIG. 4d depicts blood oxygen saturation changing process, for a typical subject in a forearm reactive hyperemia experiment.
Figure 5A:
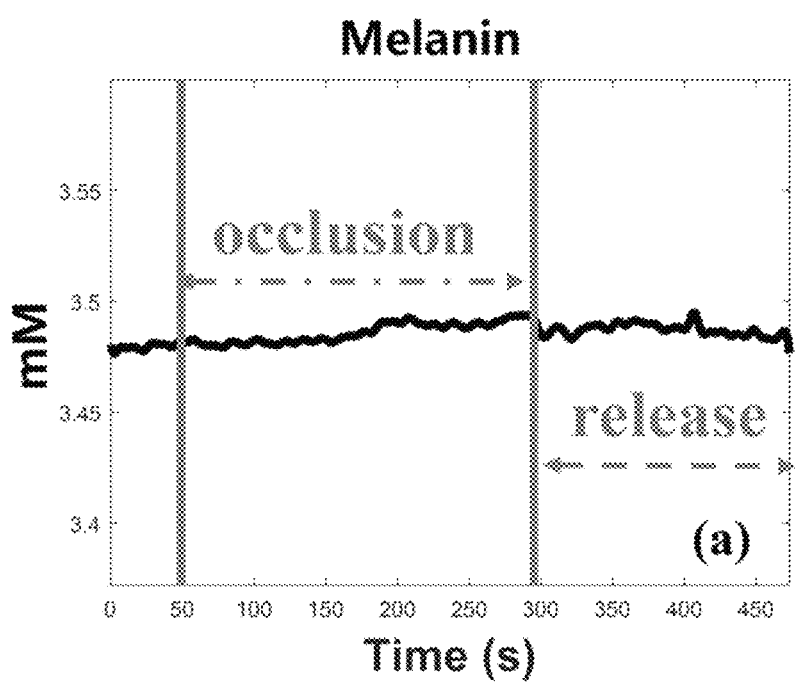
FIGS. 5a and 5b are schematic views of melanin and epidermal thickness in a forearm reactive hyperemia experiment.
Figure 5B:
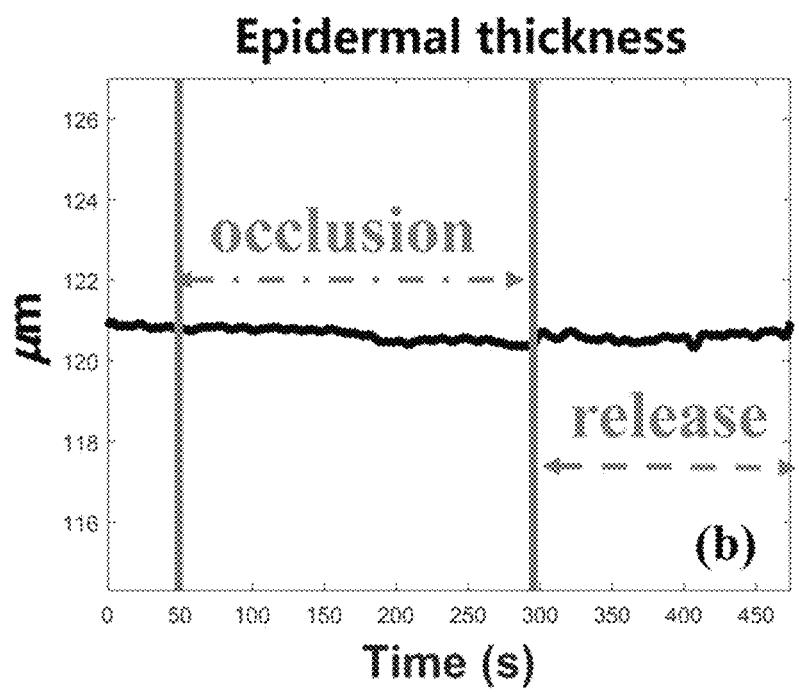
Figure 6A:
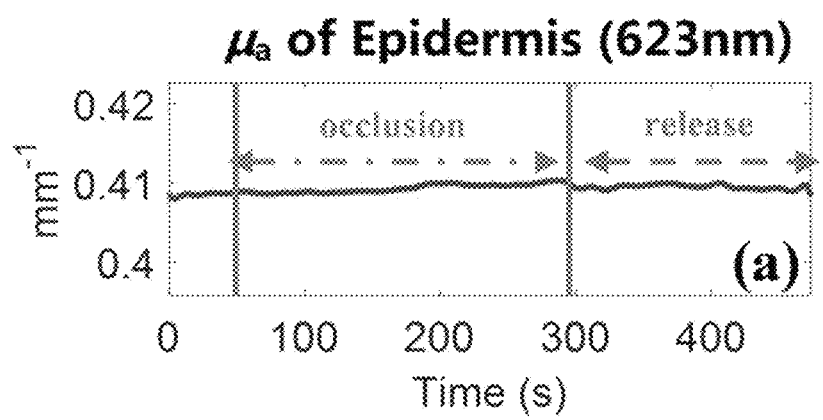
FIGS. 6a-6h are schematic views of the absorption coefficient at each wavelength of the epidermis (FIGS. 6a-6c) and dermis (FIG. 6d-6f) and the scattering coefficient (FIG. 6g) and scattering capability (FIG. 6h) of the skin.
Figure 6B:
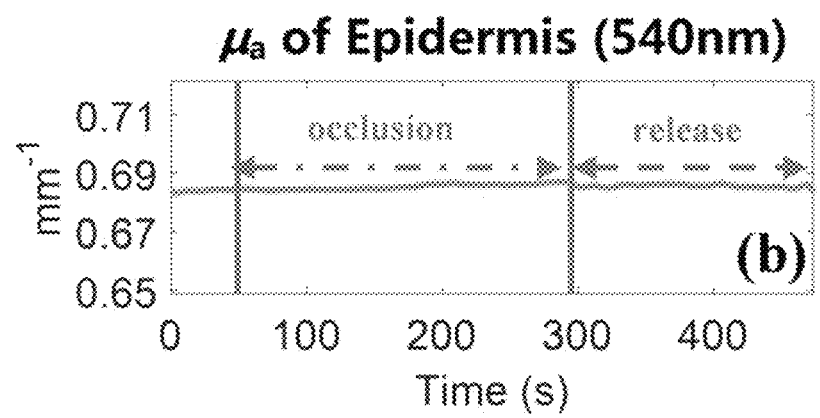
Figure 6C:
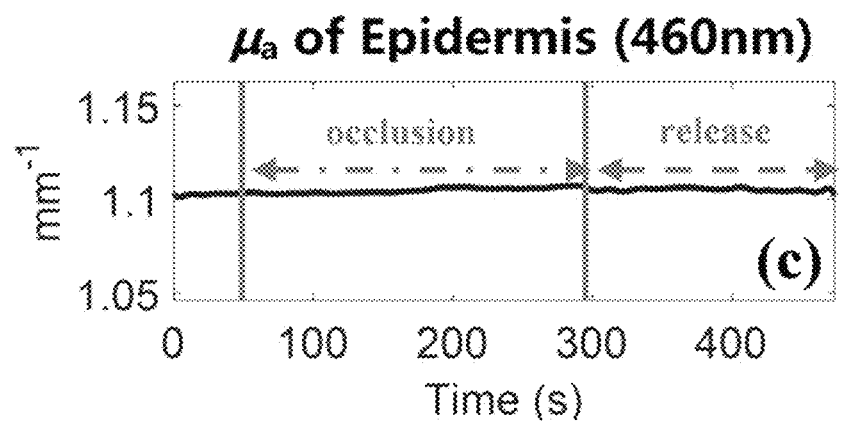
Figure 6D:
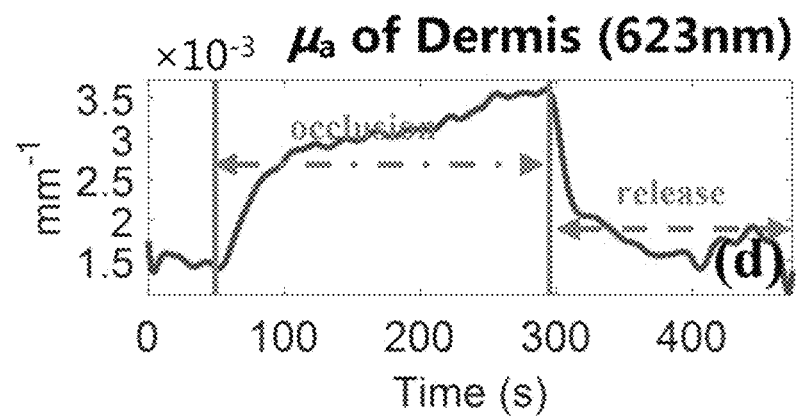
Figure 6E:
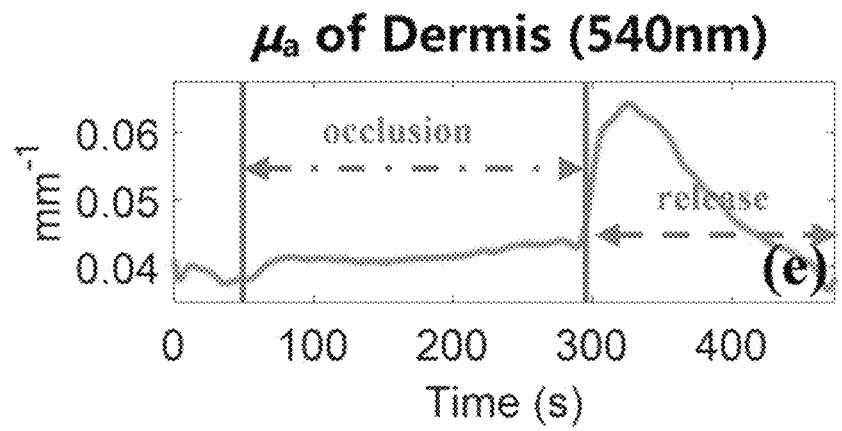
Figure 6F:
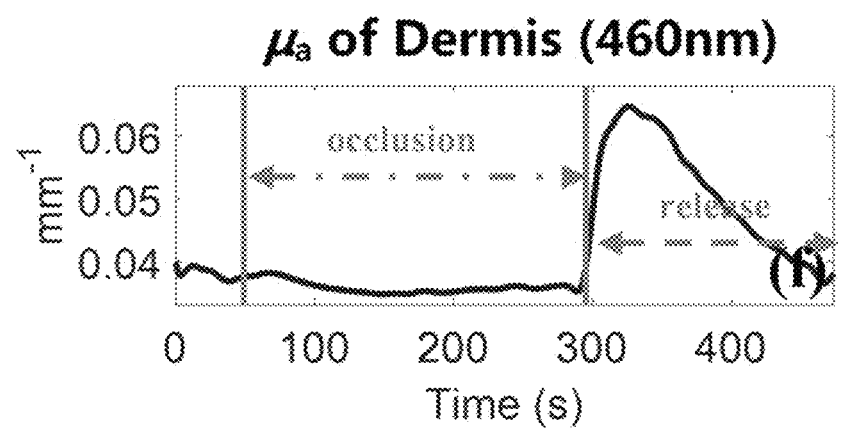
Figure 6G:
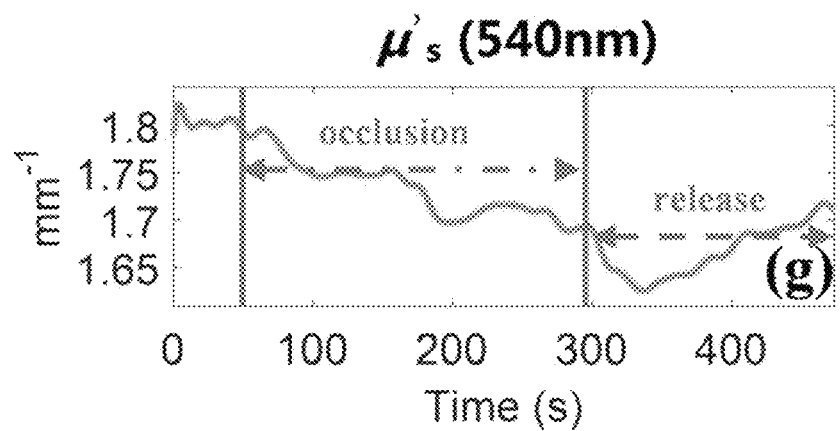
Figure 6H:
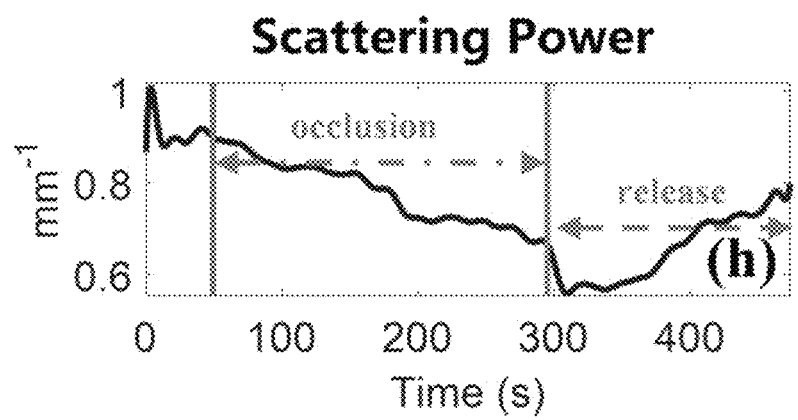

The phenomenon of the whole experiment is analyzed:

FIGS. 4a-4d show the oxyhemoglobin concentration, deoxyhemoglobin concentration, total hemoglobin concentration, and blood oxygen saturation changing process for a typical subject in a forearm reactive hyperemia experiment. When the cuff blocks venous and arterial blood flow, blood accumulates in the subcutaneous blood vessels due to distal vein occlusion, causing the blood vessels to dilate and total hemoglobin (the sum of $HbO_2$ and Hb, (FIG. 4c) to rise slightly. Vascular occlusion results in rapid consumption of oxygen in the tissue, resulting in a rapid decrease in tissue oxyhemoglobin ($HbO_2$ concentration, FIG. 4c) and an increase in tissue deoxyhemoglobin concentration (Hb, FIG. 4b). Upon cuff release, a typical hyperemia response is exhibited, with large amounts of fresh blood flowing into tissue that has been depleted of blood oxygen during occlusion. The cuff release section is shown in FIG. 4a. Tissue oxygen saturation ($StO_2$) is initially 0.82, decreased to 0.56 after cuff occlusion, and finally rapidly increased back to 0.85 after cuff release. Combined with the proper effects of the SSMD-SFDI system and the mapping model of layered structure on exfoliation of epidermal melanin (FIGS. 5a and 5b), change in dermal blood oxygen (FIG. 4), epidermal thickness and optical information of each layer (FIGS. 6a-6h) (scattering coefficient and absorption coefficient of each layer) are obtained.

Application Example 2: Detection of Physiological and Optical Information of Pigmented Nevus The pigmented nevus on the skin is detected using the SSMD-SFDI system in combination with a mapping model of layered structure.

Figure 7:
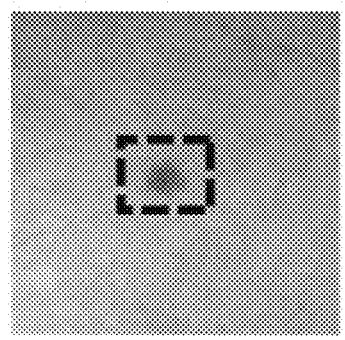
FIG. 7 shows the area under test under the SSMD-SFDI system, and the dashed rectangular area is the area of interest.
Figure 8A:
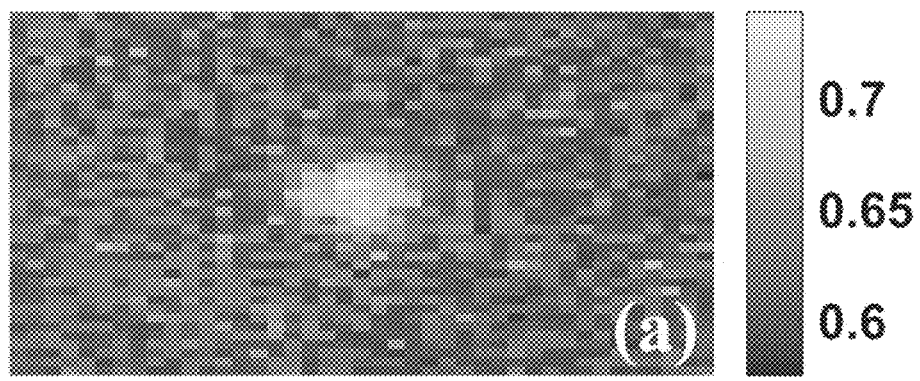
FIGS. 8a-8h are distribution diagrams of optical parameters of normal tissue and pigmented nevus (with absorption coefficients (FIGS. 8a-8f), scattering coefficient (FIG. 8g) and scattering capability (FIG. 8h) for each wavelength of each layer).
Figure 8B:
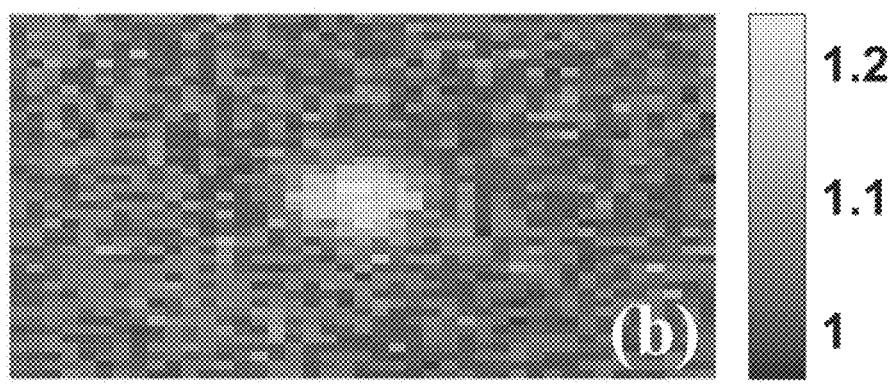
Figure 8C:
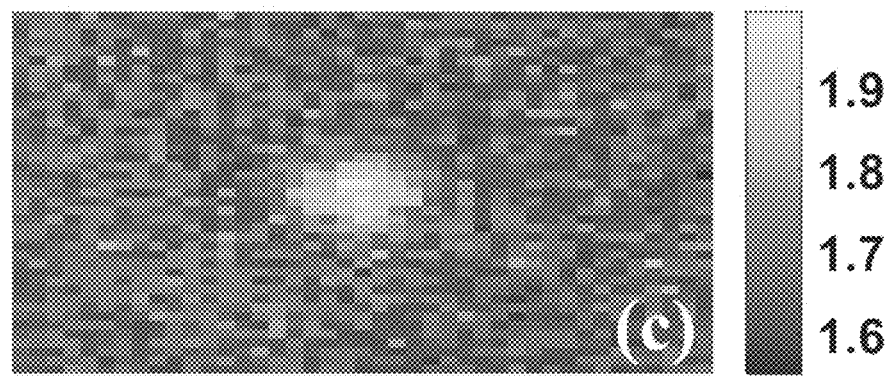
Figure 8D:
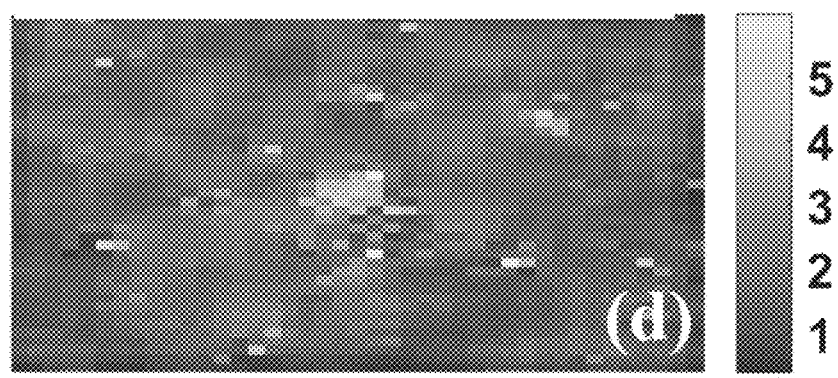
Figure 8E:
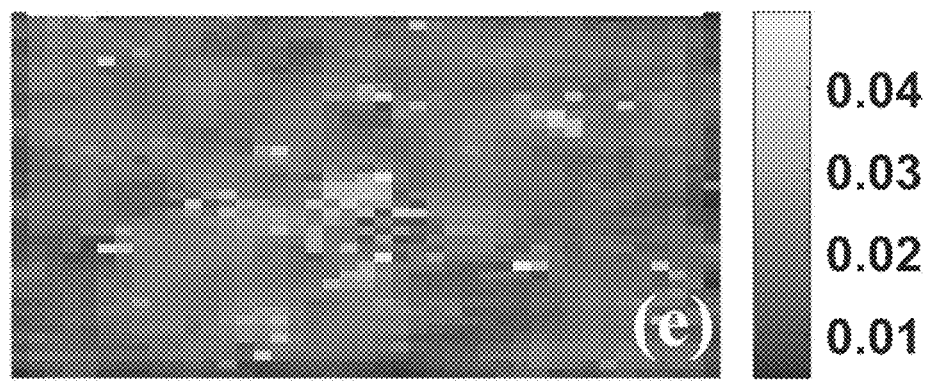
Figure 8F:
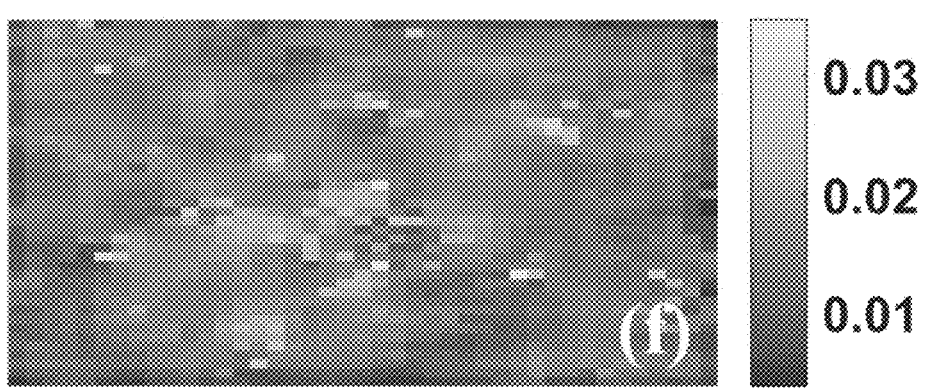
Figure 8G:
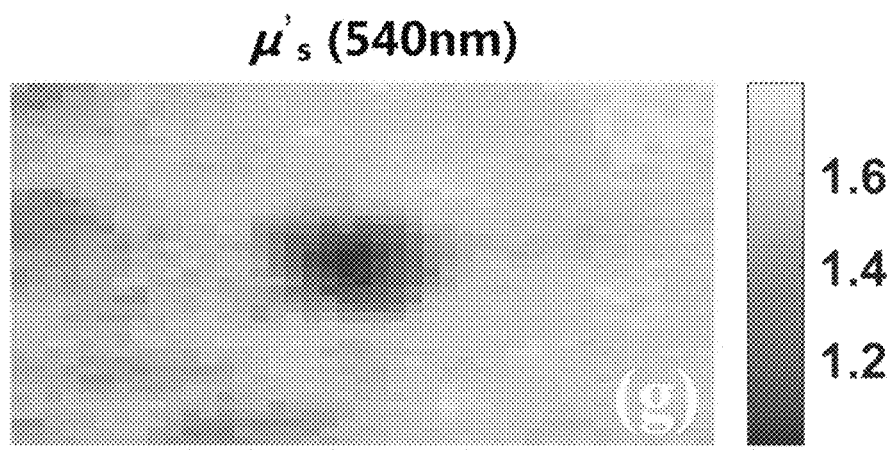
Figure 8H:
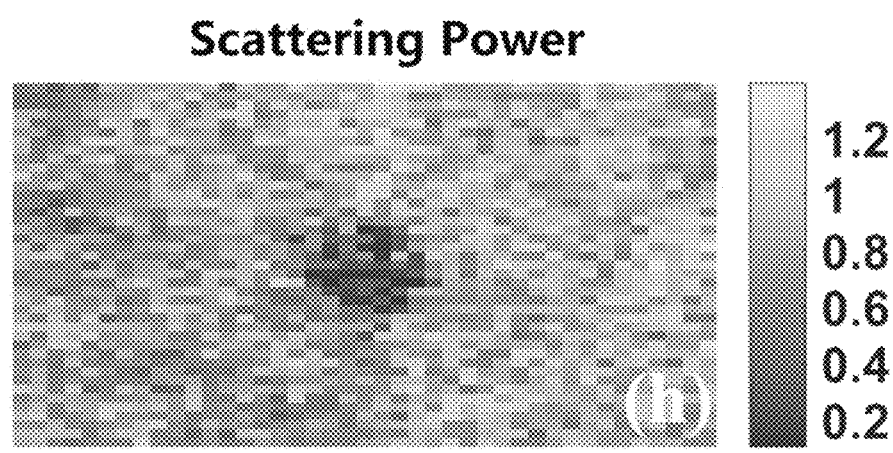
Figure 9A:
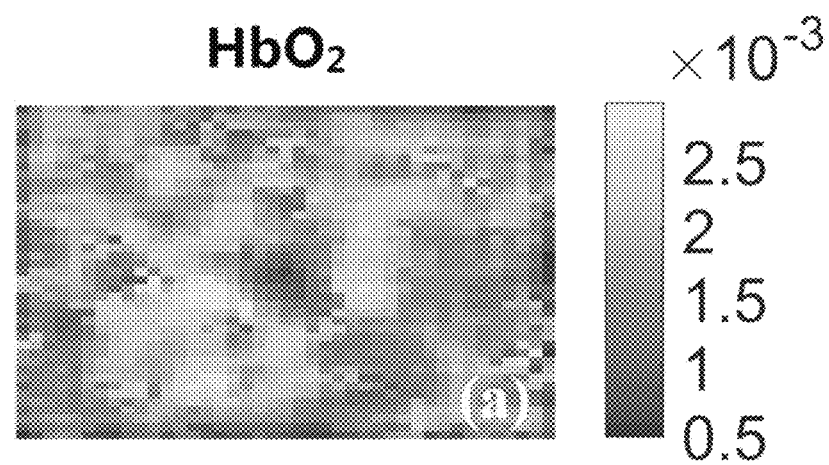
FIGS. 9a-f are distribution diagrams of physiological parameters of normal tissue and pigmented nevus (oxyhemoglobin (FIG. 9a), deoxyhemoglobin (FIG. 9b), total oxyhemoglobin (FIG. 9c), blood oxygen saturation (FIG. 9d), melanin (FIG. 9e), and epidermal thickness (FIG. 9f)).
Figure 9B:
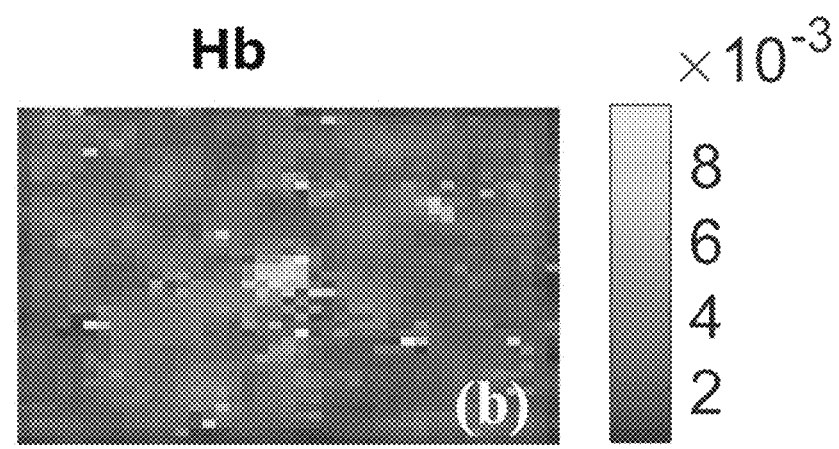
Figure 9C:
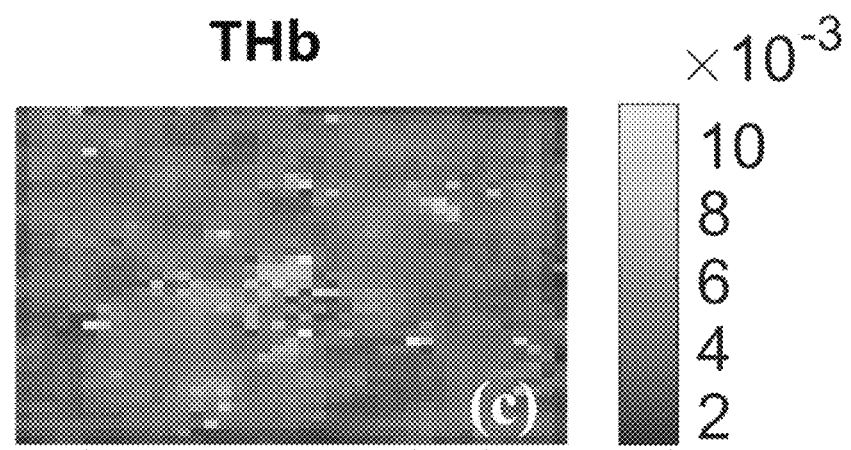
Figure 9D:
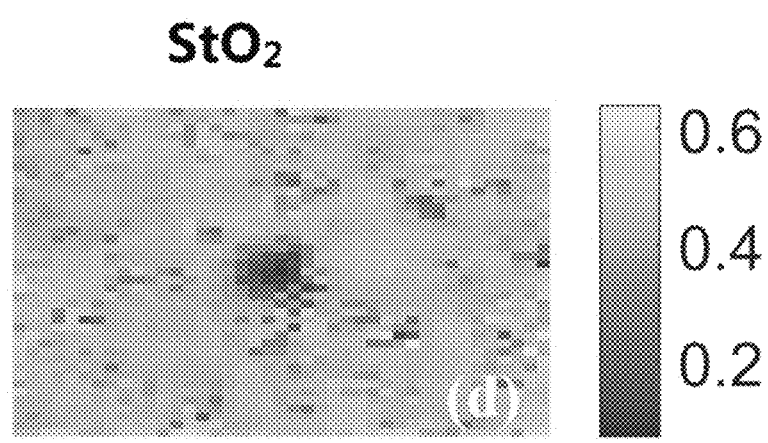
Figure 9E:
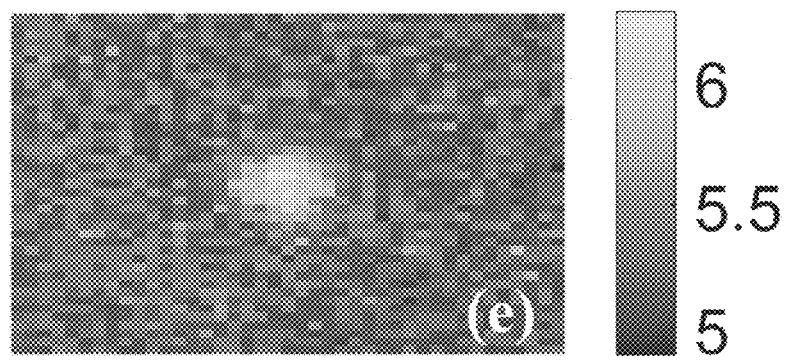
Figure 9F:
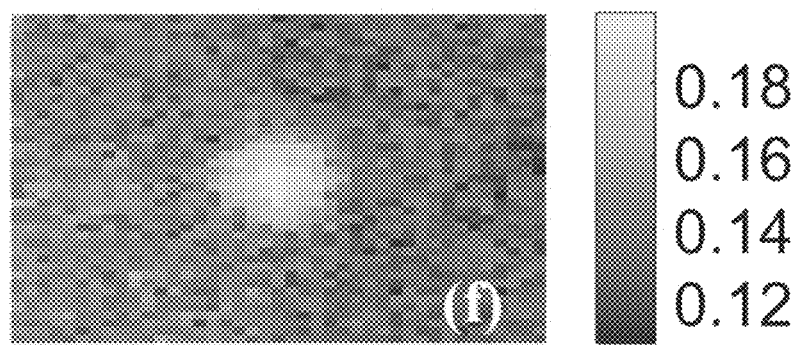

With the SSMD-SFDI system, rich optical and physiological information can be used to distinguish the pigmented nevus area with the adjacent normal area, as shown in FIG. 7.

FIGS. 8a-8h show the absorption coefficients, scattering coefficients (λ=540 nm, g) and scattering capability (FIG. 8h) of the epidermis (FIGS. 8a-8c) and dermis (FIG. 8d-8f), respectively, at each wavelength (λ=460 nm, 540 nm, 623 nm). FIGS. 9a-9f show oxyhemoglobin (FIG. 9a), deoxyhemoglobin (FIG. 9b), total hemoglobin (FIG. 9c), blood oxygen saturation (FIG. 9d), melanin (FIG. 9e), and epidermal thickness (FIG. 9f), respectively.

Through the application of two experiments, the feasibility of SSMD-SFDI system and mapping model of layered structure is fully proved, by which we can obtain real-time, continuous and 2-dimensional time variation maps of multiple physiological parameters of a regional tissue.

The examples are not to be construed as limiting the invention, and any modifications based on the spirit of the invention are intended to be within the protection scope of the invention.

The invention claimed is:

1. An optical imaging method for skin substance detection based on optical imaging and mapping a layered skin structure having an epidermis layer and a dermis layer to an equivalent uniform, non-layered medium, each layer of the layered structure defining a respective absorption coefficient and a respective scattering characteristic, the respective scattering characteristics of each layer being substantially the same, and the equivalent uniform medium defining an absorption coefficient and a scattering characteristic, the method comprising:

using large-area optical imaging to project a modulation pattern of incident light onto a surface of the skin, the modulation pattern of incident light having a plurality of wavelengths and a spatial modulation angular frequency, and to detect light reflected from the surface of the skin;

establishing the scattering characteristic of the equivalent uniform medium to be the same as the scattering characteristic of the epidermis layer and the dermis layer;

mapping the layered skin structure to the equivalent uniform medium so as to determine the respective optical parameters of the epidermis layer, dermis layer, and equivalent uniform medium, including respective absorption coefficients and scattering characteristics, by performing the steps of:

(1) establishing the absorption coefficients of epidermis and dermis as follows:

$$\mu_{a,epidermis}(\lambda)=\varepsilon_{melanin}(\lambda)c_{melanin}$$

$$\mu_{a,dermis}(\lambda)=\varepsilon_{Hb}(\lambda)c_{Hb}+\varepsilon_{HbO_2}(\lambda)c_{HbO_2},$$

wherein $c_{HbO_2}$, $c_{Hb}$ and $c_{melanin}$, are concentrations of the skin substances oxyhemoglobin, deoxyhemoglobin and melanin respectively, $\varepsilon_{HbO_2}$, $\varepsilon_{Hb}$, $\varepsilon_{melanin}$ are known molar extinction coefficients of oxyhemoglobin, deoxyhemoglobin and melanin respectively, and λ is wavelength;

(2) establishing the following relationship:

$$\mu_a(q,\lambda)L(q,\lambda)=\mu_{a,epidermis}(\lambda)h+\mu_{a,dermis}(\lambda)(L-h),$$

wherein q is incident light spatial modulation angular frequency, $\mu_a(q,\lambda)$ is the absorption coefficient of the equivalent uniform medium, h is epidermal thickness, and an average penetration depth of light $$L(q,\lambda) = \frac{(1+Ql)^2(2\mu_t')^{-2} + (1+\mu_t'l)^2(2Q)^{-2} - 2(1+Ql)(1+\mu_t'l)(Q+\mu_t')^{-2}}{(1+Ql)^2(2\mu_t')^{-1} + (1+\mu_t'l)^2(2Q)^{-1} - 2(1+Ql)(1+\mu_t'l)(Q+\mu_t')^{-1}}$$

wherein is extrapolated length, $\mu_t' \equiv \mu_a + \mu_s'$, $Q \equiv \sqrt{q^3 + 3\mu_a(\mu_a + \mu_s')}$, is extrapolated length, and $\mu_s'$ is a reduced scattering coefficient, which is a scattering characteristic;

(3) determining the absorption coefficient $\mu_a$ of the equivalent uniform medium by step (2); and obtaining a concentration of each substance oxyhemoglobin, deoxyhemoglobin and melanin respectively by Beer-Lambert law according to the determined optical parameters.

2. The method according to claim 1, further comprising using endoscopic tissue mucosal layer detection imaging to detect a skin parameter.

3. The method according to claim 1, further comprising detecting a pigmented nevus of the skin.

4. The method according to claim 1 further comprising detecting a forearm reactive hyperaemia of the skin.

5. The method according to claim 1, wherein using large-area optical imaging to project a modulation pattern of incident light onto a surface of the skin, the modulation pattern of incident light having a plurality of wavelengths and a spatial modulation angular frequency, and to detect light reflected from the surface of the skin includes using a single snapshot multiple frequency demodulation—spatial frequency domain imaging (SSMD-SFDI) system to detect and demodulate the reflected light, thereby capturing optical images of the skin.

6. The method according to claim 1, wherein using large-area optical imaging to project a modulation pattern of incident light onto a surface of the skin includes using a digital micromirror device (DMD) to project a modulation pattern onto the surface of the skin.

\* \* \* \* \*